United States Patent [19]
Chalmers et al.

[11] Patent Number: 5,595,744
[45] Date of Patent: Jan. 21, 1997

[54] RESPIRATORY DISEASE VACCINE FOR CATS

[75] Inventors: William S. K. Chalmers, St. Ives Cambs., United Kingdom; Antonius A. C. Jacobs, PS Kessel, Netherlands

[73] Assignee: Akzo Nobel N.V., Arnham, Netherlands

[21] Appl. No.: 415,783

[22] Filed: Apr. 3, 1995

Related U.S. Application Data

[63] Continuation of Ser. No. 948,196, Sep. 21, 1992, abandoned.

[30] Foreign Application Priority Data

Sep. 30, 1991 [EP] European Pat. Off. .............. 91308931

[51] Int. Cl.$^6$ .......................... A61K 39/10; A61K 39/00; A61K 39/255; A61K 39/02
[52] U.S. Cl. ..................... 424/253.1; 424/184.1; 424/240.1; 424/229.1; 424/236.1
[58] Field of Search ............................. 424/184.1, 240.1, 424/253.1, 229.1, 236.1

[56] References Cited

U.S. PATENT DOCUMENTS 4,031,204  6/1977  Davis .
4,788,056  11/1988  Lutticken et al. .
4,789,544  12/1988  Nelson et al. .

FOREIGN PATENT DOCUMENTS 0012718  6/1980  European Pat. Off. .

OTHER PUBLICATIONS

Bemis et al; Jo. Clin Microbiol Apr. 1977, pp. 471–480, vol. 5(4).
Goodnow et al; Microbiol reviews Dec. 1980 pp. 722–738, vol. 44(4).
R. D. Welsh, *J Am Anim Hosp Assoc*, 1996, 32:153–158.
Elliott. 1991. Bordetella bronchiseptica in a closed cat colony. Vet. Record. 129(21):474–475.
S. R. Creighton et al., "Bacteriologic and Cytologic Evaluation of Animals with Lower Respiratory Tract Disease Using Transtracheal Aspiration Biopsy," *Evaluation of Animals Using Transtracheal Aspiration Biopsy*, 10:227–232, May/Jun. 1974.
S. Bech–Nelson et al., "Feline Respiratory Tract Disease in Louisiana," *Am J Vet Res*, 41:8:1293–1298, Aug. 1980.
R. M. Gaskell, "Upper Respiratory Disease in the Cat Including Chlamydia: Control and Prevention," *Feline Practice*, 20:6:7–12, Nov./Dec. 1992.
K. Willoughby et al., "Isolation of *B. bronchiseptica* from Kittens with Pneumonia in a Breeding Cattery," *The Veterinary Record*, pp. 407–408, 1991.
P. Roudebush et al., "Antibacterial Susceptibility of *Bordetella bronchiseptica* Isolates from Small Companion Animals with Respiratory Disease," *Journal of the American Animal Hospital Association*, 17:793–797, Sep./Oct. 1981.
*Diseases of the Cat: Medicine and Surgery*, vol. 1, (1987), pp. 297, 317, 234 and 237, W. B. Saunders Co., Jean Holzworth, Ed.
*Feline Husbandry, Diseases and Management in the Multiple–Cat Environment*, Niels C. Pedersen, pp. 233–235, American Veterinary Publications, Inc. Paul W. Pratt, Ed., 1991.
N. Pedersen, "Chapter 23: Bordetellosis", *Feline Infectious Diseases*, pp. 153–154, American Veterinary Publications, Inc., 1988.
B. Snyder et al., "Respiratory Tract Diseases Associated with *Bordetella bronchiseptica* Infection in Cats," *J.A.V.M.A.*, pp. 293–294, Aug. 1, 1973.
S. B. Snyder et al., "Respiratory tract disease associated with *Bordetella bronchiseptica* infection in cats," Journal of the American Veterinary Medical Association, vol. 163, No. 3, pp. 293–194, Aug. 1, 1973, USA.
S. K. Fisk et al., "*Bordetella bronchiseptica* in laboratory cats from Central California", Biological Abstracts, vol. 56, p. 1497, Abstract No. 14925, Aug. 1973, USA.

*Primary Examiner*—James C. Housel
*Assistant Examiner*—N. M. Minnifield
*Attorney, Agent, or Firm*—Gregory R. Muir; William M. Blackstone

[57] ABSTRACT

The present invention is concerned with the use of *Bordetella bronchiseptica* antigens for the prevention of upper respiratory disease in cats. These antigens may also be combined with Feline herpes virus, Feline calici and/or Chamydia antigens.

6 Claims, No Drawings

RESPIRATORY DISEASE VACCINE FOR CATS

This is a continuation of application Ser. No. 07/948,196 filed Sep. 21, 1992, now abandoned.

The present invention is concerned with the use of *Bordetella bronchiseptica* antigens for the manufacture of a vaccine and with a method for the prevention of upper respiratory disease in cats.

Infections of the respiratory system of the cat are of considerable concern to small animal clinicians. Since the introduction of commercial vaccines for feline respiratory disease, the number of pet cats presented with signs of upper respiratory disease (URD) in young cats in multiple cat house-holdings or open catteries has decreased substantially. The first clinical sign observed in URD is frequently an acute attack of sneezing. This may be followed shortly by conjunctivitis with ocular discharge, rhinitis with nasal discharge, an ulcerative disease, enteritis or acute arthritis. Fever, anorexia, and depression are present in varying degrees.

Conjunctivitis is usually a striking manifestation of URD. This may begin unilaterally, but bilateral involvement within hours is the typical case. Photophobia, excess lacrimation with wetting of the face below the medial canthus of the eyes, and chemosis almost invariably occur. The ocular discharge usually changes from serous to mucoid or mucopurulent, and in many cases it becomes purulent, resulting in the formation of dried crusts around the eyes. The eyelids may become stuck together, and copious purulent discharge may accumulate in the conjunctival sac.

Concurrent with the development of conjunctivitis, rhinitis usually develops with a serous nasal discharge which later becomes mucoid or mucopurulent. As this discharge dries the nares are obstructed by the dried crusts and the cat will resort to mouth breathing. Involvement of the trachea and bronchi results in inflammatory exudate, rales, and coughing.

Excess salivation may occur in those rare cases of ulcerative stomatitis. Ulcers may occur on the tongue, the hard palate, at the angle of the jaws, and on the tip of the nose.

Up to the present invention there is a broad consensus of opinion with respect to the causative agents responsible for URD in cats. Feline herpesvirus (FHV) and Feline calicivirus (FCV) are considered to be the two main primary agents responsible for these respiratory infections in cats. In addition, it has been established that another pathogen is able to induce signs of URD in cats, i.e. Feline *Chlamydia psittaci*.

In the literature there is abundant evidence of the potency of the above pathogens to induce as a sole pathogen the clinical signs of URD in cats. Consequently, because of the recognition of this potency the immunization of cats with vaccines comprising FHV, FCV and/or Chlamydia antigens has been disclosed. See for example: Bittle, J. L. and Rubic, W. J., Am. J. Vet. Res. 36, 89, 1975; Povey, R. C. and Wilson, M. R., Feline Pract. 8, 35, 1978; Scott, F. W., Am. J. Vet. Res. 38, 229, 1977; Bittle, J. L. and Rubic, W. J., Am. J. Vet. Res. 37, 275, 1976; Gaskell, C. J. et al., Res. Vet. Sci. 32, 23, 1982; Kahn, D. E. and Hoover, E. A., Am. J. Vet. Res. 37, 279, 1976; Povey, C., Feline Pract. 7, 12, 1977; Chappuis, G. et al., Comp. Immun. Microbiol. Infect. Dis. 3, 221, 1979; Wilson, J. S. et al., Vet. Med. Small Anim. Clin. 78, 1869, 1983; Cocker, F. M. et al., Vet. Rec. 114, 353, 1984; Johnson, R. P., Res. Vet. Sci. 37, 44, 1984; Webb, P. J., Vet. Update 1, 5, 1987; Morris, T. H., Vet. Rec. 126, 250, 1990; Harbour, D. A. et al., Vet. Rec. 128, 77, 1991.

Furthermore, the Council of the American Veterinary Medical Association (AVMA) issued a revised report summarizing information available on important diseases affecting dogs and cats, and including recommendations for immunization to control these diseases. The revision was necessary to account for new knowledge and new products. The immunization guidelines for immunoprophylaxis of feline URD recommend the vaccination of cats against FHV and FCV. Whereas vaccination of cats against chlamydiosis should be done as required. These guidelines do neither consider *Bordetella bronchiseptica* as a causative agent of feline URD nor do they suggest to vaccinate cats against this pathogen (J. Am. Vet. Med. Assoc. 195, 314, 1989).

In addition, a survey of the problems met in the veterinary field, and the animal health products available for their treatment is outlined in "The Small Animal Market For Animal Health Products" (Ed.: G. Bloomfield, PJB Publications Ltd, 1990). With respect to respiratory diseases in cats, three causative agents are identified, i.e. FHV, FCV and *Chlamydia psittaci*.

This survey also includes information with respect to feline URD vaccines commercially available at that moment. All these vaccines comprise FHV, FCV and/or Chlamydia antigens, either in a modified live or inactivated form.

*Bordetella bronchiseptica* is the cause of atrophic rhinitis and pneumonia in swine.

In dogs, *Bordetella bronchiseptica* has been characterized as the primary etiological agent in infectious canine tracheobronchitis (kennel cough).

Other mammalian species are also afflicted with *Bordetella bronchiseptica* infections of the respiratory tract including laboratory animals, e.g. guinea pigs, rabbits and rats thereby producing the clinical symptoms of the infection. The prior art abundantly discloses the use of *Bordetella bronchiseptica* vaccines to be used for the prevention of respiratory disease in the animals identified above. See for example: published patent(s) application(s) U.S. Pat. Nos. 4,857,318; 4,888,169; 4,530,832; EP 72,656; DE 3,517,805; FR 2,571,618; NL 8702728; U.S. Pat. Nos. 4,456,588; 4,250,265; EP 12,718; NL 179,875; U.S. Pat. No. 4,016,253, in addition to Novotny, P. et al., Infect. Immun. 50, 190, 1985; Vernier, L. et al., Am. J. Vet. Res. 45, 2634, 1984; Sakano, T. et al., Am. J. Vet. Res. 45, 1814, 1984 and Mc Carthy, D. H. et al., Vet. Med. 79, 694, 1984. None of these publications suggests to use the respective *Bordetella bronchiseptica* vaccines for the immunoprophylaxis of feline URD.

*Bordetella bronchiseptica* is rarely reported to be isolated from cats. Switzer, W. P. et al., Am. J. Vet. res. 27, 1134, 1966, and Fisk, S. K. and Soave, O. A., Lab. Animal Sci. 23, 33, 1973 reported that *Bordetella bronchiseptica* was isolated from a small number of healthy cats. Furthermore, Snyder, S. B. et al., J. Am. Vet. Med. Assoc. 163, 293, 1973 reported that from 10 cats out of 127 cases with respiratory disease *Bordetella bronchiseptica* was isolated. In Roudebush, P. and Fales, W. M., J. Am. Anim. Hospital Assoc. 17, 793, 1981 one cat with clinical signs of respiratory disease carrying *Bordetella bronchiseptica* is described. However, in the latter two cases no attempts were made to isolate other respiratory pathogens, especially FHV, FCV and Chlamydia were not looked for and discounted as the cause of disease. In particular, it was not established in the two cases that URD could be induced by *Bordetella bronchiseptica*.

Thus, *Bordetella bronchiseptica* has not been recognized as a pathogen causing URD in cats in the field. In fact, *Bordetella bronchiseptica* has been reported to be isolatable from healthy cats (Switzer, W. P. et al., and Fisk, S. K. and Soave O. A., supra). Cats were only regarded to be carriers of *Bordetella bronchiseptica* (U.S. Pat. No. 4,530,832 and EP patent application 12,718) as opposed to other animals, particular swine and dogs, where it was established as a primary causative agent of respiratory disease. Therefore, until now one has not been motivated to vaccinate cats against *Bordetella bronchiseptica* infection.

Surprisingly, it has been found now that *Bordetella bronchiseptica* as the sole pathogen can be responsible for URD in cats, especially in field cats. Furthermore, it has been established that experimental challenge of cats with *Bordetella bronchiseptica* resulted in the appearance of clinical signs similar to URD signs noticed with cats in the field.

Therefore, the invention provides a use of *Bordetella bronchiseptica* antigens for the manufacture of a vaccine suitable for the prevention of URD in cats.

*Bordetella bronchiseptica* antigens include inactivated whole cells, i.e. bacterins, live attenuated bacteria and subunits of the *Bordetella bronchiseptica* cells, i.e. relevant antigens capable of inducing a protective immune response in inoculated animals.

For the present invention use can be made of *Bordetella bronchiseptica* vaccines already described in the prior art and/or commercially available for the prevention of respiratory tract disease in swine or dogs. Examples of such vaccines are summarized above.

In preparing the vaccine of the present invention cells of *Bordetella bronchiseptica* are introduced into a suitable culture medium, which is incubated at a temperature favouring the growth of the organism. Preferably, Tryptose Phosphate Broth (TPB) may be used for propagation of the organism. Propagation temperatures of 36° C. to 38° C. are favorable. Subsequently, the cells can be harvested from the culture medium with or without concentration of the cells by mechanical processing.

For the preparation of an inactivated vaccine the bacterial cells are killed with for example the known agents such as formaldehyde, beta-propiolactone ethylene-imine or a derivative there of, NaN3 and thimerosal.

Usually, an adjuvant and if desired one or more emulsifiers such as TWEEN, a nonionic emulsifier and "SPAN", a nonionic surfactant are also incorporated into the inactivated vaccine. Suitable adjuvants include (mineral) oil-emulsion of for example BAYOL and MARCOL (both Adjuvants) aluminium hydroxide, -phosphate or -oxide, vitamin-E acetate solubilisate or saponins.

For the live vaccine according to the invention attenuated *Bordetella bronchiseptica* bacteria are used. Attenuated bacteria may be obtained by a number of methods known in the art for this purpose, e.g. passaging the bacteria through (solid) culture medium for a sufficient number of passages, applying a mutagen including nitrosoguanidine, 5-bromouracil and ultraviolet irradiation. In this way for example temperature-sensitive (ts) mutant strains can be obtained. Examples of live attenuated vaccines are summarized above.

The vaccine according to the invention preferably comprises purified and isolated subunit antigens of *Bordetella bronchiseptica* bacteria. Examples of such subunit antigens of *Bordetella bronchiseptica* are disclosed in Novotny, P. et al., Infect. Immun. 50, 190 and 199, 1985; U.S. Pat. Nos. 4,250,265 and 4,857,318.

A preferred vaccine according to the invention makes use of the isolated fimbriae of *Bordetella bronchiseptica*.

In addition to *Bordetella bronchiseptica* subunit antigens, such a vaccine may additionally comprise an adjuvant, for example an adjuvant as metioned above.

If desired a vaccine according to the invention comprises additional pharmaceutical carriers, including stabilizers and buffers well known in the art for bacterial vaccine preparation.

Present feline URD vaccine comprising FHV, FCV and/or Chlamydia antigens either in a live attenuated or inactivated form. It is clear that a vaccine according the invention comprising *Bordetella bronchiseptica* antigens may also contain FHV, FCV and/or Chlamydia antigens. Alternatively, the vaccine according to the invention may be combined with the antigens of one or more of these other feline URD pathogens just before vaccination.

A vaccine according to the invention may further contain Feline infectious enteritis virus antigens.

The present invention also provides a vaccine kit comprising in addition to the *Bordetella bronchiseptica* vaccine one or more vaccines selected from the group consisting of FHV vaccine, FCV vaccine, Feline infectious enteritis virus and Feline Chlamydia.

The vaccine according to the invention may be administered to the cats by parenteral administration, e.g. intramuscular or subcutaneous injection or via intra-nasal, oral, intra-ocular or intra-tracheal administration.

The vaccine usually may contain $10^2$ to $10^{10}$ cells per dose or 1 to 500 µg subunit antigen per dose.

A suitable vaccination regime for the vaccine of the present invention comprises a first and second vaccination at 8–10 weeks and 12–16 weeks of age, respectively. If desired followed by yearly booster vaccination.

EXAMPLE 1

Isolation of Bordetella bronchiseptica from clinically ill cats

Twelve 6-week old SPF kittens were obtained from Hillgrove Family Farms LTD., Oxford, UK, for registration trials. Within 72 hours of arrival some of the kittens developed an acute rhinitis with accompanying clinical signs of sneezing and nasal mucopurulent discharge. Swabs were taken for both viral and bacterial culture as these kittens were to be used for Feline calicivirus and Feline herpesvirus backpassage trials. Swab material inoculated onto confluent monolayers of FEF cells failed to show any signs of FCV or FHV infection. However swab material plated onto blood agar plates and G-20G (Bordetella isolation medium) produced an abundant growth of *B. bronchiseptica* which was found to be sensitive to tetracyclin antibiotic. Aliquots of this feline Bordetella were frozen at −70° C. after subsequent passage to purify the culture. A sample was sent to Cambridge Veterinary Investigation Centre for confirmation. The organism isolated from the diseased cats was indeed indentified as *Bordetella bronchiseptica*. Initially the infected animals were treated with amoxycillin before indentification of agent and sensitivities were established. A temporary improvement was observed. Thereafter, the cats were treated with tetracyclin for a minimum period of 5 days until the infection had cleared. No further problems were encountered with this group of cats. As confirmation that the major viral causes of respiratory disease were not involved, all kittens remained sero negative for FCV and FHV antibodies. In addition there was no evidence for Chlamydial infection as tested by serology and isolation.

A Bordetella bronchiseptica strain was isolated from a throat swab taken from a 13-week-old cat designsted QQ2 which was part of a vaccine efficacy study. Cats for this study were purchased from Liberty Cattery (Liberty, N.J.). Prior to vaccination with the Tricat vaccine (Feline panleukemia virus+FCV+FHV), cats were screened for any extraneous viruses using the FEF cell line which is susceptible to a wide variety of feline viruses. No extraneous viruses were detected. Cats were vaccinated initially with the Tricat vaccine and revaccinated two months later. The white blood cell (WBC) count started to rise in cat QQ2 approximately five days post-initial vaccination. Because of the high WBC count, a bacterial infection was suspected and bacterial isolation was attempted. *Bordetella bronchiseptica* was isolated.

EXAMPLE 2

Preparation of Bordetella bronchiseptica bacterin vaccine

After aerobic growth of strain Bb-7 on bloodagar for 48 hours at 37° C., one colony was inoculated in Tryptose Phosphate Broth (TPB) and cultured aerobically at 37° C. for 24 hours. This culture was used to inoculate a larger volume of TPB (1:99) which again was cultured aerobically at 37° C. for 24 hours. After growth the culture was inactivated with 0.5% formalin (v/v). Subsequently, the culture was concentrated to $2{,}22\times10^{11}$ bacteria per ml on a HVLP 0.45μ filter. This concentrated cell suspension was used to prepare a w/o (emulsion) vaccine: $5.55\times10^9$ bacteria per gram of vaccine.

EXAMPLE 3

Preparation of Bordella bronchiseptica fimbrial subunit vaccine

A Bb-7 culture (see example 2), was inactivated with 0.02% $NaN_3$ and heated for 15 minutes at 65° C. to release the fimbriae from the cells. Subsequently, the cells were removed by continuous flow centrifugation and the supernatant containing the fimbriae was concentrated 100 fold using a PM-500 filter (Romicon). After concentration, the fimbriae were precipitated by the addition of an equal volume of a solution containing 8% PEG-8000 and 1M NaCl. This mixture was incubated for 24 hours at 4° C. after which the fimbriae were collected by centrifugation (35.000×g). The pellet was resuspended in a small volume (0.3% of initial culture volume) of 50 mM Tris-HCL bufr pH 7.5.

As a final purification step an equal volume of 1% SDS was added and the mixture was incubated for 3 hours at room temperature, after which the fimbrae were collected by centrifugation (20.000×g) and resuspended in 50 mM Tris-HCL buffer pH 7.5 containing 0.01% thiomersal and 0.07% EDTA.

The antigen concentration was determined using an enzyme immuno assay (EIA). The concentration of fimbrial antigen is expressed as EIA units (EU) per unit of volume. For final vaccine preparation antigen concentrate (10%), saline+0.01% thimerosal solution (40%) were mixed with vitamin-E acetate solubilisate (50%) until a homogeneous suspension (containing 400 EU per ml) was obtained.

EXAMPLE 4

*Bordetella bronchiseptica* challenge and vaccination experiments in cats

MATERIALS AND METHODS

Animals

To test the challenge model (exp. KCV91801), 4 eight weeks old cats (no. 125, 127, 129 and 131) were used. All 4 cats were shown to be both serologically (titre $<2^2$) and culturally (throat swab), negative to *Bordetella bronchiseptica.* For the protection experiment (exp. KCV91809) 15 four weeks old cats were used. All 15 cats were culturally negative for Bordetella, but had maternal antibodies which had decreased to $<2^2$ at day of challenge (8 weeks of age).

Vaccine

Purified *Bordetella bronchiseptica* fimbriae were prepared and mixed with adjuvant as described in Example 3. This vaccine (batch no. 710-2) contained 400 EU/ml (about 40 μg fimbrial protein per ml)

Vaccination 10 cats (4 weeks of age) were vaccinated subcutaneously with 1 ml of the vaccine, 5 cats remained as unvaccinated controls. Two weeks after priming, 10 cats (6 weeks of age) were boostered.

Challenge

At 8 weeks of age cats were challenged by aerosol exposure to a mixed culture of *Bordetella bronchiseptica* strain $D_2$ (Goodnow, R. A. et al. J. Vet. Res. 44, 207–211, 1983), strain Bb-UK-1 and strain Bb-USA-1. The mixed culture was prepared by mixing equal volumes of the three cultures each containing $0.5–1.0\times10^{10}$ cfu/ml). Groups of 4 (exp. KCV91801) or 15 (exp. KCV91809) cats were placed in a closed isolator (of about 0.7×0.7×1.0 m) and exposed to an aerosol of the mixed Bordetella culture (approximately 20 ml of the mixed culture) using a DeVilbiss 65 nebulizer. The cats remained in the isolator for 30 minutes. The whole procedure was carried out in a Hepa-filtered room at reduced pressure.

Bacterial cultures

*Bordetella bronchiseptica* strain $D_2$, Bb-UK-1 and Bb-USA-1 were cultured in TPB (100 ml TPB in cotton wool plugged 1000 ml flasks) under vigorous agitation at 37° C. for 24 hours.

Serology

Blood samples were taken prior to challenge in exp. KCV91801 and 1 week before priming (3 weeks of age), at day of priming (4 weeks of age) at day of booster (6 weeks of age) and at day of challenge (8 weeks of age) in exp. KCV91809.

The Bordetella antibody titre was determined in an ELISA system.

Bacterial reisolation

Throat swabs were collected at post-challenge day −1, 4, 6, 11 and 14 in exp. KCV91801 and at post-challenge day −1, 5, 8, 12, 15, 18, 22 and 29 in exp. KCV91809. Throat swabs were vortexed in 2 ml of 0.85% NaCl and serial 10 fold dilutions were plated out on bloodagar.

Clinical examination

Cats were examined at the day before challenge and for up to two weeks post-challenge (until clinical signs subsided) and scored in a numerical clinical scoring system (Table 1).

RESULTS

Within 3–6 days post-challenge (Exp. KCV91801), all four cats developed signs of upper respiratory disease, characterized by rhinitis, sneezing, coughing, trachea and larynx sensitive to palpation and dry or moist rales at auscultation (see Table 2–5 individual cat scores). Furthermore, *Bordetella bronchiseptica* was reisolated in high numbers from throat swabs (Table 6).

The cats used in exp. KCV91809 were obtained from three litters. The three mother cats had low Bordetella antibody titres which had been transferred to the kittens (in utero and colostrum). The kittens stayed with their mother and received milk until six weeks of age. At 4 weeks of age (day of priming) maternal antibodies had decreased (all cats to be vaccinated had a titre of $<2^2$). At six weeks of age (two weeks postpriming and day of booster), vaccinated cats had responded to the first vaccination (mean titre of $2^{3.1}$) while the control cats had a low maternal antibody titre which had decreased further (Table 7). At 8 weeks of age all vaccinates had high titres (mean titre of $2^{9.5}$) while the maternal antibodies of the control cats had decreased to $<2^2$. Furthermore, all cats were shown to be culturally negative to Bordetella bronchiseptica at the day before challenge. In addition, no local reactions were observed at 1 or 2 weeks post booster vaccination. One day before challenge all cats were clinically examined and appeared all healthy and in a good condition.

Four to five days post-challenge, all five control cats had developed signs of upper respiratory disease as found in exp. KCV91801 (Table 8–12). The signs of repiratory disease were present for about 2 weeks after which the signs subsided. In contrast vaccinated cats were (almost) completely free from clinical signs. Total numerical clinical scores are summarized in Table 13. Protection against clinical signs was as follows: spontaneous or induced coughing (protection 95%), sneezing (protection 5%), dry or moist rales (protection 100%). If all parameters are considered, an overall protection of 98% was found (Table 13).

The bacterial reisolation data are shown in Table 14. The first two weeks (when clinical signs were present in the controls) there was no apparent reduction in bacterial counts in the vaccinates compared to the controls. Thereafter, vaccinates cleared the bacteria compared to the controls which remained at a high level, resulting in a reduction of about 80% at day 15 and 18 post-challenge and a reduction of 99% at day 22 and 29 post-challenge.

In conclusion, the results show that *Bordetella bronchiseptica* can act as a primary pathogen in cats resulting in signs of URD and that the vaccine (400 EU/ml dose) protects against these signs of upper respiratory disease, induced by *Bordetella bronchiseptica* as the sole pathogen.

TABLE 1

| Numerical clinical scoring system | |
|---|---|
| General Impression | 0 = active |
| | 1 = depressed |
| | 2 = depressed + loss of appetite |
| | 3 = depressed + laying often |
| Eyes | 0 = normal |
| | 1 = clear discharge |
| | 2 = mucop. discharge |
| Nose | 0 = normal |
| | 1 = clear discharge |
| | 2 = mucop. discharge |
| Throat | 0 = normal |
| | 1 = slight pharyngitis |
| | 2 = severe pharyngitis |
| Sneezing | 0 = normal |
| | 1 = slight sneezing |
| | 2 = severe sneezing |
| Respiration | 0 = normal |
| | 1 = spontaneous coughing slight |
| | 2 = spontaneous coughing severe |
| | 3 = dyspnoe |
| | 4 = dyspnoe + abdominal resp. |
| Palpation larynx | 0 = normal |
| | 1 = slight coughing |
| | 2 = severe coughing |
| Palpation trachea | 0 = normal |
| | 1 = slight coughing |
| | 2 = severe coughing |
| Auscultation | 0 = normal |
| | 1 = slight dry rales |
| | 2 = severe dry rales |
| | 3 = moist rales |
| | 4 = solid areas (no sound) |

TABLE 2

NUMERIC CLINICAL SCORES KCV 91801
Cat no. 125

| | day post-challenge | | | | | | | | | | | | | | | | Total per |
|---|---|---|---|---|---|---|---|---|---|---|---|---|---|---|---|---|---|
| parameter | −1 | 0 | 1 | 2 | 3 | 4 | 5 | 6 | 7 | 8 | 9 | 10 | 11 | 12 | 13 | 14 | parameter |
| General Impression | | | | | | | | | | | | | | | | | |
| Eyes | | | | | | | | | | | | | | | | | |
| Nose | | | | | | | | 1 | | | | 1 | 1 | 1 | 1 | | 5 |
| Throat | | | | | | | | | | | | | | | | | |
| Sneezing | | | | | | 1 | | | 1 | | | | | | | | 2 |
| Respiration | | | | | | 1 | | 1 | | | | | | | | | 2 |
| Palpation larynx | | | | | | | 1 | | | | | | | | | | 1 |
| Palpation traches | | | | | | | | | | 1 | | | | | | | 1 |
| Auscultation | | | | | | | | | | | | | | | | | |
| Total per day | | 0 | | | 0 | 0 | 2 | 0 | 2 | 1 | 1 | 1 | 1 | 1 | 1 | 1 | 11 |

TABLE 3

NUMERIC CLINICAL SCORES KCV 91801
Cat no. 127

| parameter | -1 | 0 | 1 | 2 | 3 | 4 | 5 | 6 | 7 | 8 | 9 | 10 | 11 | 12 | 13 | 14 | Total per parameter |
|---|---|---|---|---|---|---|---|---|---|---|---|---|---|---|---|---|---|
| General Impression | | | | | | | | | | | | | | | | | |
| Eyes | | | | | | | | | | | | | | | | | |
| Nose | | | | | | | | 1 | 1 | | | 1 | | | | | 3 |
| Throat | | | | | | | | | | | | | | | | | |
| Sneezing | | | | | | | 1 | 1 | 1 | | | 1 | | | | | 4 |
| Respiration | | | | | | | 1 | | | 1 | | | | | | | 2 |
| Palpation larynx | | | | | | | | | | | | | | | | | |
| Palpation traches | | | | | | | | | 1 | | | | 1 | | | | 2 |
| Auscultation | | | | | | | | | | | | | 1 | | | | 1 |
| Total per day | | 0 | | | 0 | 0 | 2 | 2 | 3 | 1 | 0 | 2 | 2 | 0 | 0 | 0 | 12 |

TABLE 4

NUMERIC CLINICAL SCORES KCV 91801
Cat no. 129

| parameter | -1 | 0 | 1 | 2 | 3 | 4 | 5 | 6 | 7 | 8 | 9 | 10 | 11 | 12 | 13 | 14 | Total per parameter |
|---|---|---|---|---|---|---|---|---|---|---|---|---|---|---|---|---|---|
| General Impression | | | | | | | | | | | | | | | | | |
| Eyes | | | | | | | | | | | | | | | | | |
| Nose | | | | | | 1 | 1 | 1 | 1 | | | | | | | | 4 |
| Throat | | | | | | | | | | | | | | | | | |
| Sneezing | | | | | | | | | 1 | | 1 | | | | | | 2 |
| Respiration | | | | | 1 | 1 | 1 | 1 | 1 | | | | | | | | 5 |
| Palpation larynx | | | | | | | | | | | | | | | | | |
| Palpation traches | | | | | | 1 | | 1 | | | | | | | | | 2 |
| Auscultation | | | | | | | | 1 | 1 | | | | | | | | 2 |
| Total per day | | 0 | | | 1 | 3 | 2 | 4 | 4 | 0 | 1 | 0 | 0 | 0 | 0 | 0 | 15 |

TABLE 5

NUMERIC CLINICAL SCORES KCV 91801
Cat no. 131

| parameter | -1 | 0 | 1 | 2 | 3 | 4 | 5 | 6 | 7 | 8 | 9 | 10 | 11 | 12 | 13 | 14 | Total per parameter |
|---|---|---|---|---|---|---|---|---|---|---|---|---|---|---|---|---|---|
| General Impression | | | | | | | | | | | | | | | | | |
| Eyes | | | | | | | | | | | | | | | | | |
| Nose | | | | | | | | | | | | | 1 | | | | 1 |
| Throat | | | | | | | | | | | | | | | | | |
| Sneezing | | | | | | | | 1 | | | | 1 | | | | | 2 |
| Respiration | | | | | | | | | | | | 1 | | | | | 1 |
| Palpation larynx | | | | | | | | | | | | | | | | | |
| Palpation traches | | | | | | | | | | | | | | | | | |
| Auscultation | | | | | | | | 1 | | | | 1 | | 1 | | | 3 |
| Total per day | | 0 | | | 0 | 0 | 0 | 2 | 0 | 0 | 0 | 3 | 1 | 1 | 0 | 0 | 7 |

TABLE 6

Reisolation data from throat swabs (exp. KCV91801)
nd = not determined

| | Bacteriological counts from throat swabs in 10 log at post-challenge day | | | |
|---|---|---|---|---|
| cat no. | 4 | 6 | 11 | 14 |
| 125 | 4.2 | 4.7 | nd | 4.4 |
| 127 | 3.5 | 5.0 | nd | 4.8 |
| 129 | 4.3 | 5.0 | 3.5 | nd |
| 131 | 4.2 | 4.0 | 3.0 | 3.3 |
| mean | 4.1 | 4.7 | 3.3 | 4.2 |

TABLE 7

Bordetella antibody titres (2 log) at T = −1 week, day of priming, day of booster and day of challenge (exp. KCV91809) V = Vaccinate, C = Control

| | Bordetella antibody titre (2 log) at | | | |
|---|---|---|---|---|
| Cat No. | T = −1 week (age 3 weeks) | day of priming (age 4 weeks) | day of booster (age 6 weeks) | day of challenge (age 8 weeks) |
| 1 V | 1.9 | 1.7 | 3.1 | >12 |
| 2 V | 2.2 | 1.8 | 1.7 | 8.9 |
| 3 V | 2.4 | 1.8 | 2.4 | 8.8 |
| 4 V | 1.5 | 1.1 | 1.7 | 9.8 |
| 5 V | 1.9 | 1.8 | 3.0 | 8.8 |
| 6 V | 2.0 | 1.9 | 2.9 | 10.2 |
| 7 V | 2.8 | 1.9 | 3.3 | 8.8 |
| 8 V | 3.8 | 1.9 | 3.6 | 9.9 |
| 9 V | 2.7 | 1.2 | 6.2 | 8.8 |
| 10 V | 1.4 | 1.8 | 2.8 | 9.3 |
| mean V | 2.3 | 1.7 | 3.1 | >9.5 |
| 11 C | 1.7 | <1 | <1 | <1 |
| 12 C | 1.9 | 3.0 | 2.8 | 1.2 |
| 13 C | 3.2 | 3.4 | 3.0 | 1.8 |
| 14 C | 3.6 | 3.5 | 2.5 | 1.5 |
| 16 C | 3.8 | 2.9 | 2.6 | 1.7 |
| mean C | 2.8 | <2.8 | <2.4 | <1.4 |

TABLE 8

NUMERIC CLINICAL SCORES KCV 91809
Cat no. 11

| | day post-challenge | | | | | | | | | | | | | | | | | Total per parameter |
|---|---|---|---|---|---|---|---|---|---|---|---|---|---|---|---|---|---|---|
| parameter | −1 | 0 | 1 | 2 | 3 | 4 | 5 | 6 | 7 | 8 | 9 | 10 | 11 | 12 | 13 | 14 | 15 | |
| General Impression | | | | | | | | | | | | | | | | | | |
| Eyes | | | | | | | | | | | | | | | | | | |
| Nose | | | | | | | | | | | | | | | | | | |
| Throat | | | | | | | | | | | | | | | | | | |
| Sneezing | | | | | | | | | 1 | 2 | 1 | 1 | 1 | | 1 | | | 7 |
| Respiration | | | | | | 1 | 1 | 1 | | | 1 | | | | | | | 4 |
| Palpation larynx | | | | | | | | | 1 | 1 | 1 | 1 | | | | | | 4 |
| Palpation traches | | | | | | | | | 1 | | | | | | | | | 1 |
| Auscultation | | | | | | 1 | 1 | 1 | 2 | 2 | 2 | 1 | | | 1 | | | 11 |
| Total per day | | 0 | | | | 2 | 2 | 2 | 5 | 5 | 5 | 3 | 1 | 0 | 2 | 0 | 0 | 27 |

60

TABLE 9

NUMERIC CLINICAL SCORES KCV 91809
Cat no. 12

| parameter | -1 | 0 | 1 | 2 | 3 | 4 | 5 | 6 | 7 | 8 | 9 | 10 | 11 | 12 | 13 | 14 | 15 | Total per parameter |
|---|---|---|---|---|---|---|---|---|---|---|---|---|---|---|---|---|---|---|
| General Impression | | | | | | | | | | | | | | | | | | |
| Eyes | | | | | | | | | | | | | | | | | | |
| Nose | | | | | | | | | | | | | | | | | | |
| Throat | | | | | | | | | | | | | | | | | | |
| Sneezing | | | | | | | | | 1 | 2 | | | | 1 | | | | 4 |
| Respiration | | | | | | | | | | | | | | | | | | |
| Palpation larynx | | | | | | | 1 | | | | | | | | | | | 1 |
| Palpation traches | | | | | | | | | | | | | | | | | | |
| Auscultation | | | | | | | | 1 | 1 | 1 | 1 | | | | | | | 4 |
| Total per day | 0 | | | | | 0 | 0 | 2 | 2 | 3 | 1 | 0 | 0 | 1 | 0 | 0 | 0 | 9 |

TABLE 10

NUMERIC CLINICAL SCORES KCV 91809
Cat no. 13

| parameter | -1 | 0 | 1 | 2 | 3 | 4 | 5 | 6 | 7 | 8 | 9 | 10 | 11 | 12 | 13 | 14 | 15 | Total per parameter |
|---|---|---|---|---|---|---|---|---|---|---|---|---|---|---|---|---|---|---|
| General Impression | | | | | | | | | | | | | | | | | | |
| Eyes | | | | | | | | | | | | | | | | | | |
| Nose | | | | | | | | 1 | 1 | | | | | | | | | 2 |
| Throat | | | | | | | | | | | | | | | | | | |
| Sneezing | | | | | | | 1 | 2 | 2 | 1 | 2 | 2 | | | | | | 10 |
| Respiration | | | | | | | | 1 | 1 | | | | | | | | | 2 |
| Palpation larynx | | | | | | | | 1 | 2 | 1 | 1 | | 1 | | | | | 6 |
| Palpation traches | | | | | | | | 1 | | | | | | | | | | 1 |
| Auscultation | | | | | | | | 3 | 3 | 1 | 1 | 1 | 1 | | | | | 10 |
| Total per day | 0 | | | | | 0 | 1 | 9 | 9 | 3 | 4 | 3 | 2 | 0 | 0 | 0 | 0 | 31 |

TABLE 11

NUMERIC CLINICAL SCORES KCV 91809
Cat no. 14

| parameter | -1 | 0 | 1 | 2 | 3 | 4 | 5 | 6 | 7 | 8 | 9 | 10 | 11 | 12 | 13 | 14 | 15 | Total per parameter |
|---|---|---|---|---|---|---|---|---|---|---|---|---|---|---|---|---|---|---|
| General Impression | | | | | | | | | | | | | | | | | | |
| Eyes | | | | | | | | | | | | | | | | | | |
| Nose | | | | | | | | | | | | | | | | | | |
| Throat | | | | | | | | | | | | | | | | | | |
| Sneezing | | | | | | | 2 | 1 | | 1 | 1 | | | | 1 | 1 | | 7 |
| Respiration | | | | | | 1 | 1 | | | | | | | | | | | 2 |
| Palpation larynx | | | | | | 1 | 1 | 1 | 1 | 1 | 1 | 1 | 1 | | 1 | 1 | 1 | 11 |
| Palpation traches | | | | | | 1 | | | | 1 | | | | | | | | 2 |
| Auscultation | | | | | | 1 | | | | 2 | 1 | 1 | | | | 1 | | 6 |
| Total per day | 0 | | | | | 4 | 4 | 2 | 1 | 5 | 3 | 2 | 1 | 0 | 2 | 3 | 1 | 28 |

TABLE 12

NUMERIC CLINICAL SCORES KCV 91809
Cat no. 16

| parameter | -1 | 0 | 1 | 2 | 3 | 4 | 5 | 6 | 7 | 8 | 9 | 10 | 11 | 12 | 13 | 14 | 15 | Total per parameter |
|---|---|---|---|---|---|---|---|---|---|---|---|---|---|---|---|---|---|---|
| General Impression | | | | | | | | | | | | | | | | | | |
| Eyes | | | | | | | | | | | | | | | | | | |
| Nose | | | | | | | | | 1 | | | | | | | | | 1 |
| Throat | | | | | | | | | | | | | | | | | | |
| Sneezing | | | | | | | | 2 | 2 | 2 | 1 | | | | | 1 | | 9 |
| Respiration | | | | | | | 1 | | | | | | | | | | | 1 |
| Palpation larynx | | | | | | | | | | | | 1 | 1 | 1 | | | | 3 |
| Palpation traches | | | | | | | | | | | | | | | | | | |
| Auscultation | | | | | | | | | 1 | 1 | 1 | 1 | 1 | | | | | 5 |
| Total per day | | 0 | | | | | 0 | 1 | 3 | 4 | 3 | 3 | 2 | 2 | 0 | 0 | 1 | 0 | 19 |

TABLE 13

Summarizing Table of total numerical clinical scores (exp. KCV91809) V = Vaccinate, C = Control

| Cat No. | -1 | 4 | 5 | 6 | 7 | 8 | 9 | 10 | 11 | 12 | 13 | 14 | 15 | total |
|---|---|---|---|---|---|---|---|---|---|---|---|---|---|---|
| 1 V | | | | | | | | | | | | | | 0 |
| 2 V | | | | | | | | | | | | | | 0 |
| 3 V | | | | | | | | | | | | | | 0 |
| 4 V | | | 1 | | | | | | | | | | | 1 |
| 5 V | | | | | | | | | | | | | | 0 |
| 6 V | | | | | | | | | | | | | | 0 |
| 7 V | | | | | | | | | | | | | | 0 |
| 8 V | | | | | | | | | | | | | | 0 |
| 9 V | | | | | | | | | 1 | | | | | 1 |
| 10 V | | | 2 | | | | | | | | | | | 2 |
| mean V | 0 | 0 | 0.2 | 0.1 | 0 | 0 | 0 | 0 | 0.1 | 0 | 0 | 0 | 0 | 0.4 |
| 11 C | | 2 | 2 | 2 | 5 | 5 | 5 | 3 | 1 | | 2 | | | 27 |
| 12 C | | | | 2 | 2 | 3 | 1 | | | 1 | | | | 9 |
| 13 C | | | 1 | 9 | 9 | 3 | 4 | 3 | 2 | | | | | 31 |
| 14 C | | 4 | 4 | 2 | 1 | 5 | 3 | 2 | 1 | | 2 | 3 | 1 | 28 |
| 16 C | | | 1 | 3 | 4 | 3 | 3 | 2 | 2 | | | 1 | | 19 |
| mean C | 0 | 1.2 | 1.6 | 3.6 | 4.2 | 3.8 | 3.2 | 2.0 | 1.2 | 0.2 | 0.8 | 0.8 | 0.2 | 22.8 |
| % protection | | 100 | 87 | 97 | 100 | 100 | 100 | 100 | 92 | 100 | 100 | 100 | 100 | 98 |

TABLE 14

Reisolation data from throat swabs (exp. KCV91809)

| Cat No. | vaccination status | Bacteriological counts from throat swabs in 10 log at post-challenge day | | | | | | | |
|---|---|---|---|---|---|---|---|---|---|
| | | -1 | 5 | 8 | 12 | 15 | 18 | 22 | 29 |
| 1 | vaccinate | <1 | 4.5 | 4.5 | 4.8 | 5.0 | 4.7 | <1 | 1.3 |
| 2 | vaccinate | <1 | 5.4 | 3.9 | 3.1 | 3.5 | 4.6 | 1.7 | 3.5 |
| 3 | vaccinate | <1 | <1.0 | 2.0 | 5.1 | 4.2 | 6.0 | 2 | 3.5 |
| 4 | vaccinate | <1 | 3.0 | 4.4 | 3.5 | 3.4 | 4.5 | 4.1 | |
| 5 | vaccinate | <1 | 4.7 | 4.9 | 2.9 | 2.8 | 4.5 | 3.1 | 4.1 |
| 6 | vaccinate | <1 | <1.0 | 3.0 | 5.2 | 4.8 | 4.7 | 4.5 | 3.1 |
| 7 | vaccinate | <1 | 4.5 | 3.6 | 3.9 | 4.2 | 4.9 | 3.0 | 4.1 |
| 8 | vaccinate | <1 | 2.5 | 2.8 | 3.2 | 4.2 | 5.7 | 2.3 | 3.0 |
| 9 | vaccinate | <1 | 3.7 | 5.0 | 3.9 | 4.3 | 6.1 | 5.2 | 4.0 |
| 10 | vaccinate | <1 | 3.5 | 2.6 | 3.8 | 4.5 | 5.2 | 5.3 | 3.9 |

TABLE 14-continued

| | | Reisolation data from throat swabs (exp. KCV91809) | | | | | | | |
|---|---|---|---|---|---|---|---|---|---|
| Cat No. | vaccination status | Bacteriological counts from throat swabs in 10 log at post-challenge day | | | | | | | |
| | | −1 | 5 | 8 | 12 | 15 | 18 | 22 | 29 |
| mean | vaccinate | <1 | 3.3 | 3.7 | 3.9 | 4.1 | 5.1 | 3.3 | 3.3 |
| 11 | control | <1 | 4.1 | 3.6 | 4.3 | 4.4 | 5.8 | 5.6 | 5.4 |
| 12 | control | <1 | 4.0 | 3.1 | 2.4 | 3.7 | 5.9 | 5.7 | 5.8 |
| 13 | control | <1 | 3.2 | 4.3 | 3.2 | 6.1 | 5.0 | 3.2 | 4.3 |
| 14 | control | <1 | 4.2 | 4.7 | 4.2 | 4.7 | 5.7 | 6.0 | 4.4 |
| 15 | control | <1 | 4.6 | 2.4 | 2.6 | 5.6 | 6.1 | 5.5 | 4.9 |
| mean | control | <1 | 4.0 | 3.6 | 3.3 | 4.9 | 5.7 | 5.2 | 5.0 |
| mean reduction vaccinates (inv log) | | 0× | 5× | 0× | −4× | 6× | 4× | 79× | 50× |
| mean % reduction vaccinates | | | | 0 | | 83 | 75 | 99 | 98 |

We claim:

1. A method for the prevention of upper respiratory disease in cats caused by Bordetella bronchiseptica acting as a sole pathogen comprising administering a vaccine for developing immunity in the upper respiratory tract comprising an effective amount of Bordetella bronchiseptica antigens to cats.

2. A method according to claim 1 wherein the vaccine comprises fimbriae as the antigens.

3. A method according to claim 1 wherein the vaccine comprises bacterins as the antigens.

4. A method according to claim 1 wherein the vaccine comprises live attenuated bacteria as the antigens.

5. A method according to claim 7 wherein the vaccine further comprises one or more antigens selected from the group consisting of:

a. *Feline herpesvirus antigens*, b. *Feline calicivirus antigens*, c. *Chlamydia psittaci* antigens, and d. Feline infectious enteritis virus antigens.

6. A method according to claim 5 wherein the vaccine comprises Feline infectious enteritis virus antigens.

* * * * *

UNITED STATES PATENT AND TRADEMARK OFFICE
CERTIFICATE OF CORRECTION

PATENT NO. : 5,595,744
DATED : January 21, 1997
INVENTOR(S) : Chalmers et al.

It is certified that error appears in the above-indentified patent and that said Letters Patent is hereby corrected as shown below:

Column 18,
Claim 5, line 1, delete "7" and replace with -- 1 --.

Signed and Sealed this

First Day of April, 1997

Attest:

BRUCE LEHMAN

Attesting Officer

Commissioner of Patents and Trademarks